United States Patent [19]

Saito et al.

[11] Patent Number: 4,514,418
[45] Date of Patent: Apr. 30, 1985

[54] 2,2-DIHALOGENO-3,3-DIMETHYLCYCLO-PROPANE DERIVATIVE FUNGICIDES

[75] Inventors: Junichi Saito, Mitaka; Shinzo Kagabu, Hachioji, both of Japan

[73] Assignee: Nihon Tokushu Noyaku Seizo K.K., Tokyo, Japan

[21] Appl. No.: 483,410

[22] Filed: Apr. 8, 1983

[30] Foreign Application Priority Data

Apr. 20, 1982 [JP] Japan .................................. 57-64701

[51] Int. Cl.³ ..................... A01N 37/00; A01N 47/46; A01N 41/02; C07C 69/00
[52] U.S. Cl. .................. 514/508; 260/453.4; 260/454; 260/456 R; 260/456 NS; 260/464; 514/514; 514/519; 514/521; 514/709
[58] Field of Search .............. 424/302, 303, 304, 298; 260/454, 456 R, 464, 453.4, 456 NS

[56] References Cited

U.S. PATENT DOCUMENTS 3,367,957  2/1968  Newallis et al. ................. 260/454
3,598,868  8/1971  Cram et al. ..................... 260/454

Primary Examiner—Alan Siegel
Attorney, Agent, or Firm—Sprung, Horn, Kramer & Woods

[57] ABSTRACT

A 2,2-dihalogeno-3,3-dimethylcyclopropylmethyl derivative of the formula

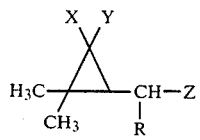

in which
X and Y each independently is halogen,
R is a hydrogen atom or a methyl group,
Z is a cyano group, a thiocyano group, a group of the formula

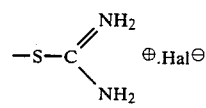

or a group of the formula

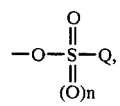

Hal is a halogen atom,
n is 0 or 1, and
Q is a lower alkyl group, a halo-lower alkyl group, a phenyl group, or a phenyl group substituted by at least one of halogen, lower alkyl and nitro, which is an intermediate in further syntheses to produce biologically active substances such as insecticides and which is itself fungicidally active.

13 Claims, No Drawings

2,2-DIHALOGENO-3,3-DIMETHYLCYCLOPROPANE DERIVATIVE FUNGICIDES

DETAILED DESCRIPTION OF THE INVENTION

This invention relates to novel 2,2-dihalogeno-3,3-dimethylcyclopropane derivatives.

More specifically, this invention relates to 2,2-dihalogeno-3,3-dimethylcyclopropane derivatives represented by the following formula:

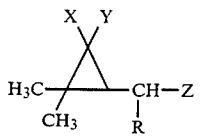
(I)

wherein X and Y each represent a halogen atom; R represents a hydrogen atom or a methyl group; and Z represents a cyano group, a thiocyano group, a group of the formula

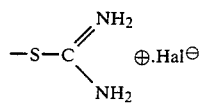

in which Hal represents a halogen atom, or a group of the formula

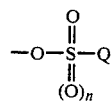

in which n is 0 or 1, and Q represents a lower alkyl group which may be substituted by a halogen atom, or a phenyl group which may be substituted by at least one member selected from the class consisting of halogen atoms, lower alkyl groups and nitro groups.

The present inventors have studied the synthesis and use of novel cyclopropane derivatives, and found that the 2,2-dihalogeno-3,3-dimethylpropane derivatives of general formula (I) are useful as biologically active substances and also as intermediates for the production of novel biologically active substances.

The present inventors have found that the compounds of this invention are novel substances not described in the prior literature, and by utilizing their high reactivity, are expected to be useful as fine chemicals typified by agricultural chemicals and medicines, for example cyclopropane alkylating agents, and materials for the synthesis of cyclopropanealkylsulfinyl derivatives, cyclopropanealkylsulfonyl derivatives, cyclopropanealkylmercaptan derivatives, cyclopropanealkylamine derivatives and cyclopropane acetic acid derivatives.

It has also been found that the compounds of the invention themselves have a fungicidal efficacy.

The utility of the compounds of this invention as described above will be more apparent from the following description.

As was disclosed in Japanese patent application No. 85657/1981, 2,2-dichloro-3,3-dimethylcyclopropylmethyl benzoate which can be synthesized for example by the reaction of a 2,2-dichloro-3,3-dimethylcyclopropylmethyl substituted-sulfonate in accordance with this invention, such as 2,2-dichloro-3,3-dimethylcyclopropylmethyl p-toluenesulfonate, with sodium benzoate, and its derivative, 2,2-dichloro-3,3-dimethylcyclopropylmethyl substitute-benzoate exhibit an excellent control effect against rice blast.

Similarly, 2,2-dichloro-3,3-dimethylcyclopropylmethyl 2-pyridinecarboxylate which can be synthesized for example by the reaction of a 2,2-dichloro-3,3-dimethylcyclopropylmethyl p-toluenesulfonate of this invention with sodium 2-pyridinecarboxylate exhibits an excellent control effect against rice blast.

Furthermore, 2,2-dichloro-3,3-dimethylcyclopropylacetonitrile, 2,2-dichloro-3,3-dimethylcyclopropylmethyl thiocyanate and S-(2,2-dichloro-3,3-dimethylcyclopropylmethyl)isothiuronium halide, which are other compounds of this invention, have an excellent control effect against rice blast.

The compounds of this invention can be produced, for example, by the following processes: (i), (ii), (iii) and (iv)).

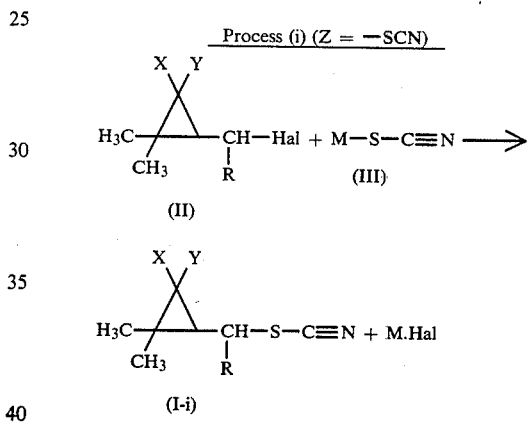

In the above reaction scheme, X and Y represent a halogen atom such as fluoro, chloro, bromo or iodo; R represents a hydrogen atom or a methyl group; Hal specifically represents the same halogen atom as above, and M represents an alkali metal atom such as lithium, sodium and potassium.

Specific examples of compounds of general formula (II) as materials for production of compounds of general formula (I-i) of this invention are as follows:

1-Chloromethyl-2,2-dichloro-3,3-dimethylcyclopropane, 1-bromomethyl-2,2-dichloro-3,3-dimethylcyclopropane, 1-β-chloroethyl-2,2-dichloro-3,3-dimethylcyclopropane, 1-β-bromoethyl-2,2-dichloro-3,3-dimethylcyclopropane, 1-chloromethyl-2-bromo-2-chloro-3,3-dimethylcyclopropane, and 1-bromomethyl-2-bromo-2-chloro-3,3-dimethylcyclopropane.

Examples of compounds of general formula (III) are potassium thiocyanate and sodium thiocyanate.

By a typical example, process (i) will be described specifically.

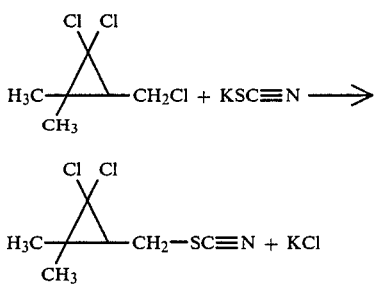

Desirably, process (i) is performed by using a solvent or a diluent, and for this purpose, all inert solvents and diluents can be used. Examples of such inert solvents or diluents include water; aliphatic, alicyclic and aromatic hydrocarbons (which may optionally be chlorinated), such as hexane, cyclohexane, petroleum ether, ligroin, benzene, toluene, xylene, methylene chloride, chloroform, carbon tetrachloride, ethylene chloride trichloroethylene and chlorobenzene; ethers such as diethyl ether, methyl ethyl ether, di-isopropyl ether, dibutyl ether, propylene oxide, dioxane and tetrahydrofuran; ketones such as acetone, methyl ethyl ketone, methyl isopropyl ketone, and methyl isobutyl ketone; nitriles such as acetonitrile, propionitrile and acrylonitrile; alcohols such as methanol, ethanol, isopropanol, butanol and ethylene glycol; esters such as ethyl acetate and amyl acetate; acid amides such as dimethylformamide and dimethylacetamide; sulfones and sulfoxides such as dimethyl sulfoxide and sulfolane; and bases such as pyridine.

The reaction can be carried out over a wide temperature range. Generally, it can be carried out at a temperature between about −20° C. and the boiling point of the mixture, desirably at a temperature between about 0° C. and about 100° C. Desirably, the reaction is carried out under atmospheric pressure. It is also possible to operate under elevated or reduced pressures.

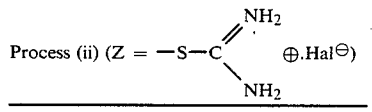

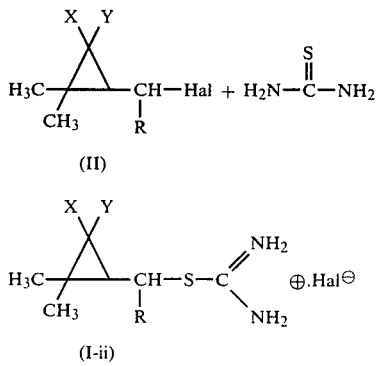

In the above reaction scheme, X, Y, R and Hal are as defined hereinabove.

Examples of compounds of general formula (II) as a material for the production of the compound of general formula (I-ii) in accordance with this invention are the same as given hereinabove.

By a typical example, process (ii) will be specifically described.

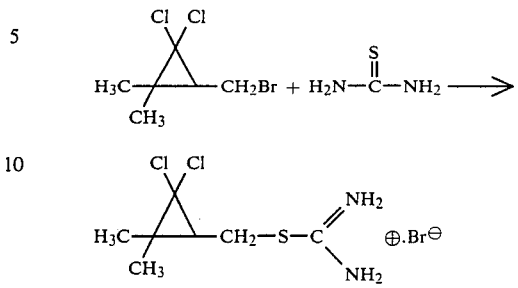

The above process may be practiced preferably by using the same inert solvent or diluent as exemplified with respect to process (i) to give the desired product of high purity in a high yield.

The reaction can be carried out over a wide temperature range, for example, at a temperature between about −20° C. to the boiling point of the mixture, desirably at a temperature between about 0° C. and about 100° C. The reaction is desirably carried out under atmospheric pressure, but if desired, it is possible to operate at elevated or reduced pressures.

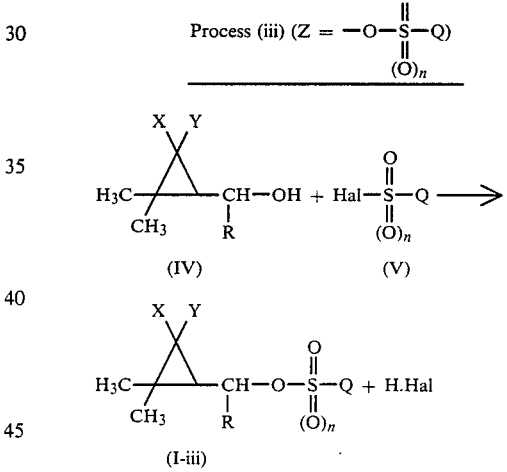

In the above scheme, X, Y, R, Q, n and Hal are as defined hereinabove.

In the above scheme, Q preferably represents a lower alkyl group, such as methyl, ethyl, propyl, isopropyl, or n-(iso-, sec-, or tert-)butyl, which may be substituted by a halogen atom such as fluoro, chloro, bromo or iodo, or a phenyl group which may be substituted by one member of the class consisting of the same halogen atoms and lower alkyl groups as above and nitro groups.

Specific examples of compounds of general formula (IV) as a material for the production of compounds of general formula (I-iii) in accordance with this invention include 2,2-dichloro-3,3-dimethylcyclopropane methanol, 1-(2,2-dichloro-3,3-dimethylcyclopropane)ethanol, and 2-bromo-2-chloro-3,3-dimethylcyclopropane methanol.

Specific examples of compounds of general formula (V) as starting material include methanesulfonyl chloride, ethanesulfonyl chloride, propane-2-sulfonyl chloride, butanesulfonyl chloride, chloromethanesulfonyl chloride, benzenesulfonyl chloride, p-toluenesulfonyl chloride, 4-chlorobenzenesulfonyl chloride, 3-nitrobenzenesulfonyl chloride, and 4-chlorobenzenesulfonyl chloride. There can also be cited the corresponding bromides.

By a typical example, process (iii) of the invention will be described specifically.

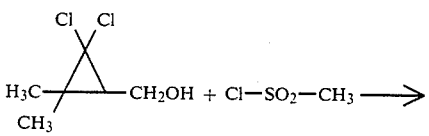

Preferably, the above process is practiced by using the same inert solvents or diluents as exemplified hereinabove to give the desired product of high purity in a high yield. The reaction can be carried out in the presence of an acid binder. Examples of the acid binder are hydroxides, carbonates, bicarbonates and alcoholates of alkali metals, or tertiary amines such as triethylamine, diethylaniline or pyridine, which are commonly used.

The reaction can be carried out over a wide temperature range. Generally, it can be carried out at a temperature between about −20° C. and the boiling point of the mixture, desirably at a temperature between about −10° C. and about 30° C. Desirably, the reaction is carried out under atmospheric pressure, but it is also possible to operate under elevated or reduced pressures.

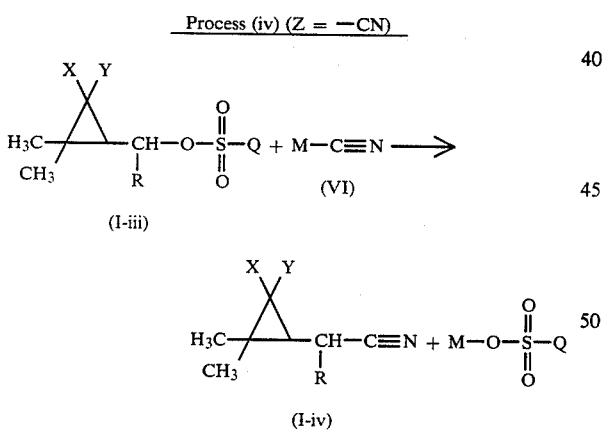

In the above scheme, X, Y, R, Q, n and M are as defined hereinabove.

The compound of general formula (I-iii) used as a starting material for the compound of general formula (I-iv) in accordance with this invention can be produced, for example, by the same procedure as shown in process (iii) described above. Specific examples include:
2,2-dichloro-3,3-dimethylcyclopropylmethyl p-toluenesulfonate,
2,2-dichloro-3,3-dimethylcyclopropylmethyl benzenesulfonate,
1-(2,2-dichloro-3,3-dimethylcyclopropyl)ethyl p-toluenesulfonate,
1-(2,2-dichloro-3,3-dimethylcyclopropyl)ethyl benzenesulfonate,
2,2-dichloro-3,3-dimethylcyclopropylmethyl methanesulfonate, and
1-(2,2-dichloro-3,3-dimethylcyclopropyl)ethyl methanesulfonate.

Specific examples of the compound of general formula (VI) as a material include sodium cyanide and potassium cyanide.

By a typical example, process (iv) be described below specifically.

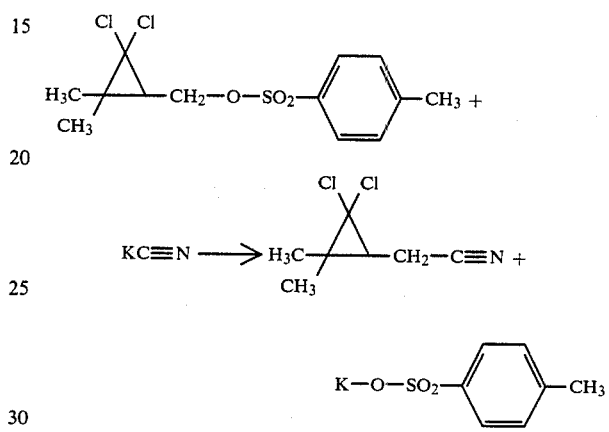

The above process can be practiced preferably by using the same inert solvents or diluents as exemplified hereinabove with respect to process (i) to give the desired product of high purity in a high yield.

The reaction can be carried out over a wide temperature range, for example at a temperature between about −20° C. and the boiling point of the mixture, desirably at a temperature between about 0° and about 100° C. Desirably, the reaction is carried out under atmospheric pressure, but it is also possible to operate at an elevated or reduced pressure.

Typical examples of the compounds of this invention are shown below together with examples of their production.

SYNTHESIS EXAMPLE 1

(Compound No. 1)

1.87 g of 2,2-dichloro-3,3-dimethyl-1-chloromethylcyclopropane and 1.0 g of potassium thiocyanate were suspended in 20 ml of ethanol, and the suspension was refluxed for 12 hours. Ethanol was evaporated, and 20 ml of water was added. The mixture was extracted with toluene. The toluene layer was washed with water and dried over sodium sulfate. The toluene was then evaporated under reduced pressure to give 1.80 g of 2,2-dichloro-3,3-dimethylcyclopropylmethyl thiocyanate, the desired compound shown above. The boiling point of the product was 115° C. at 200 mmHg.

SYNTHESIS EXAMPLE 2

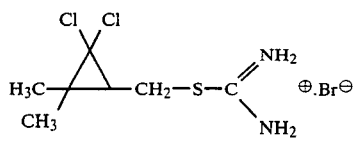 (Compound No. 2)

23.2 g of 2,2-dichloro-3,3-dimethyl-1-bromomethylcyclopropane and 8.3 g of thiourea were refluxed in 20 ml of ethanol for 30 hours. The reaction mixture was cooled. The crystals precipitated were collected by filtration, washed with diethyl ether, and dried to give 10.1 g of S-(2,2-dichloro-3,3-dimethylcyclopropylmethyl)isothiouronium bromide, the desired compound shown above. The melting point of the product was above 200° C. (decomp.).

SYNTHESIS EXAMPLE 3

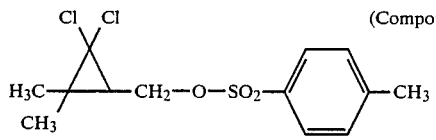 (Compound No. 3)

A solution of 33.8 g of 2,2-dichloro-3,3-dimethylcyclopropane methanol in 200 ml of pyridine was cooled to 0° C., and 38.2 g of p-toluenesulfonyl chloride was added portionwise. The reaction mixture was left to stand for 12 hours in a refrigerator (0° C.), and then poured into 1 liter of ice water. The crystals precipitated were collected by filtration, washed with water, dried in the air, and washed with hexane to give 62 g of 2,2-dichloro-3,3-dimethylcyclopropylmethyl p-toluenesulfonate, the desired compound shown above. The melting point of the product was 96.5° to 97.5° C.

By similar methods to Synthesis Example 3, the compounds of the invention shown in Table 1 were synthesized.

TABLE 1

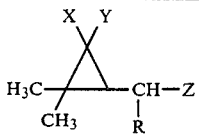

| Compound No. | X | Y | R | Z | Physical constant |
|---|---|---|---|---|---|
| 4 | Cl | Cl | H | —O—S(=O)(=O)—CH$_3$ | mp. 53–54° C. |
| 5 | Cl | Cl | H | —O—S(=O)(=O)—C$_2$H$_5$ | $n_D^{20}$1.4822 |
| 6 | Cl | Cl | H | —O—S(=O)(=O)—C$_3$H$_7$—n | $n_D^{20}$1.4819 |

TABLE 1-continued

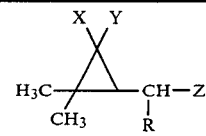

| Compound No. | X | Y | R | Z | Physical constant |
|---|---|---|---|---|---|
| 7 | Cl | Cl | H | —O—S(=O)(=O)—C$_3$H$_7$—iso | $n_D^{20}$1.4818 |
| 8 | Cl | Cl | H | —O—S(=O)(=O)—C$_4$H$_9$—n | $n_D^{20}$1.4814 |
| 9 | Cl | Cl | H | —O—S(=O)(=O)—CH$_2$Cl | $n_D^{20}$1.4822 |
| 10 | Cl | Cl | H | —O—S(=O)(=O)—C$_6$H$_5$ | mp. 42–43° C. |
| 11 | Cl | Cl | H | —O—S(=O)(=O)—C$_6$H$_4$—Cl | mp. 87–89° C. |
| 12 | Cl | Cl | H | —O—S(=O)(=O)—C$_6$H$_4$—NO$_2$ | $n^{20}$1.4963 |
| 13 | Cl | Cl | —CH$_3$ | —O—S(=O)(=O)—CH$_3$ | mp. 65–66° C. |
| 14 | Cl | Cl | —CH$_3$ | —O—S(=O)(=O)—C$_2$H$_5$ | mp. 45–47° C. |
| 15 | Cl | Cl | —CH$_3$ | —O—S(=O)(=O)—C$_4$H$_9$—n | mp. 28° C. |
| 16 | Cl | Cl | —CH$_3$ | —O—S(=O)(=O)—CH$_2$Cl | $n^{20}$1.4821 |
| 17 | Cl | Cl | —CH$_3$ | —O—S(=O)(=O)—C$_6$H$_5$ | mp. 52–54° C. |
| 18 | Cl | Cl | —CH$_3$ | —O—S(=O)(=O)—C$_6$H$_4$—CH$_3$ | mp. 85–86° C. |
| 19 | Cl | Cl | —CH$_3$ | —O—S(=O)(=O)—C$_6$H$_4$—Cl | mp. 62–63° C. |

TABLE 1-continued $$\underset{CH_3}{\overset{X\ \ Y}{H_3C\diagdown\!\!\!\diagup}}\!\!-\!\!\underset{R}{CH}\!-\!Z$$

| Compound No. | X | Y | R | Z | Physical constant |
|---|---|---|---|---|---|
| 20 | Cl | Cl | H | 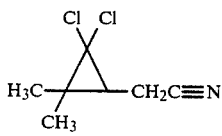 | bp. 170° C./ 0.4 mmHg |

SYNTHESIS EXAMPLE 4

$$\underset{CH_3}{\overset{Cl\ \ Cl}{H_3C\diagdown\!\!\!\diagup}}\!\!-\!\!CH_2C\!\equiv\!N$$

(Compound No. 21)

6.48 g of 2,2-dichloro-3,3-dimethylcyclopropylmethyl p-toluenesulfonate and 2.0 g of potassium cyanide were suspended in 20 ml of dimethyl formamide, and the mixture was heated at 100° C. for 24 hours with stirring. After cooling, 50 ml of water was added to the reaction mixture. The mixture was extracted with hexane. The hexane layer was washed with water, and dried over sodium sulfate. After drying, the hexane was evaporated under reduced pressure to give 3.8 g of 2,2-dichloro-3,3-dimethylcyclopropylacetonitrile, the desired compound shown above. The boiling point of the product was 96° to 98° C. at 14 mmHg.

The active compounds according to the invention exhibit an action and can therefore be employed in practice for combating undesired fungi. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as, for example, against the powdery mildew of barley causative organism (*Erysiphe graminis*), and for combating rice diseases, such as, for example, *Pyricularia oryzae*, for combating Sphaerotheca species, such as, for example, the powdery mildew of cucumber causative organism (*Spaerotheca fuliginea*) and for combating Phytophora species, such as, for example, against the late blight of tomato causative organism (*Phytophthora infestans*).

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, (liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellant, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs and azo metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and other growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, brushing on and the like. It is also possible to apply the active compounds by the ultra-low volume process or to inject the preparation of active compound or the active compound itself into the soil. The seeds of the plants can also be treated.

When using the materials according to the invention as fungicides, the amount used can be varied within a substantial range depending on the mode of application. Thus, in the treatment of parts of plants, the active compound concentrations in the use forms are in general between 1 and 0.0001% by weight, preferably between 0.5 and 0.001% by weight. In the treatment of seed, amounts of active compound of 0.001 to 50 g per kg of seed, preferably 0.01 to 10 g, are generally required. For the treatment of soil, active compound concentrations of 0.00001 to 0.1% by weight, preferably of 0.0001 to 0.02%, are required at the place of action.

The active compounds are also useful as intermediates in making other compounds which are also fungicidally active as is shown in the following examples:

SYNTHESIS EXAMPLE 5

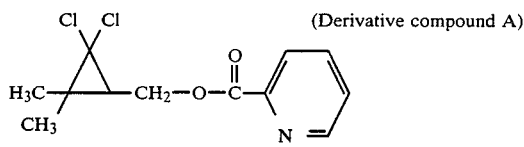

(Derivative compound A)

3.23 g of 2,2-dichloro-3,3-dimethylcyclopropylmethyl p-toluenesulfonate and 1.5 g of 2-pyridinecarboxylic acid were heated at reflux in 40 ml of a toluene solution containing 1.0 g of potassium hydroxide, 1.0 g of potassium carbonate and 50 mg of triethylbenzylammonium chloride for 12 hours. After cooling, the toluene insolubles were filtered off and washed with 30 ml of toluene; and the filtrate was washed successively with a 1% sodium carbonate aqueous solution, 20 ml of a 0.5% hydrochloric acid aqueous solution and water, and dried over anhydrous sodium sulfate. The toluene was distilled off under reduced pressure, and the residual liquid was distilled under vacuum to obtain 2.2 g of the desired product, 2,2-dichloro-3,3-dimethylcyclopropylmethyl pyridine-2-carboxylate, mp. 56° C.

Derivative compound B was synthesized by the same method as above.

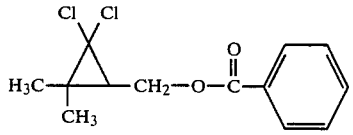

bp. 142°-145° C./0.5 mmHg.

TEST EXAMPLE 1

Effect test by water surface application of the under-mentioned liquid against rice blast Preparation of the compound to be tested:
Active compound: 50% by weight
Carrier: 45 parts of a (1:5) mixture of diatomite and kaolin
Emulsion: 5 parts of polyoxyethylene alkylphenylether The above-mentioned amounts of the active compound, carrier and emulsion are ground and mixed together to form a wettable powder and a determined amount of the powder is diluted with water to obtain the desired test compound.

Test Method:

Paddy-rice plants (kind: Asahi) were cultivated by flooding, separating the plants into each three roots, in a pot made of white porcelain having a diameter of 12 cm, and at the initial stage of separation of roots, a liquid compound with a prescribed concentration prepared as above, was poured upon water until the dosage of the applied compound reached the indicated one, taking care that the liquid compound does not splash directly the above-ground parts of the rice plants. 4 days thereafter, a suspension of spores of rice blast fungi was inoculated to the paddy-rice plants by spraying in a conventional way and the paddy-rice plants were kept in an inoculation room maintained at a temperature of 23°-25° C. and at a relative humidity of 100% for 24 hours. Then the pots for paddy-rice plants were transferred into a glass hothouse at a temperature of 20°-28° C., and 7 days after the inoculation, the disease incidence rate per pot was classified and evaluated, and further the control proportion (%) was obtained.

| Disease incidence rate | Proportion of diseased speck area (%) |
| --- | --- |
| 0 | 0 |
| 0.5 | 2 or less |
| 1 | 3–5 |
| 2 | 6–10 |
| 3 | 11–20 |
| 4 | 21–40 |
| 5 | 41 or more |

Control proportion (%) =

$$\left( \frac{\frac{\text{Disease incidence}}{\text{rate of the non-}} - \frac{\text{Disease incidence}}{\text{rate of the}}}{\text{applied section}} \right) \times 100$$

In the present test, the results obtained for 3 pots per section are shown.

The results are illustrated in Table 2.

TABLE 2

| Compounds No. | Amounts of effective ingredients mg/m² | Control proportions % | Phytotoxocity |
| --- | --- | --- | --- |
| 1 | 800 | 95 | — |
| 2 | " | 95 | — |
| 21 | " | 95 | — |
| Derivative compounds | | | |
| A | 800 | 100 | — |
| B | " | 95 | — |

Note
1. The symbol "—" in the column of phytotoxicity shows that there was no phytotoxicity.
2. Derivative compounds A: 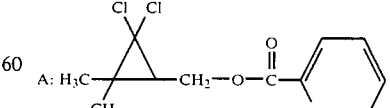

B: 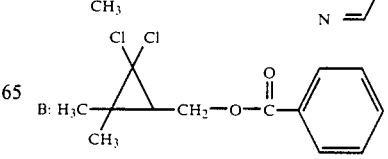

What is claimed is:

1. A 2,2-dihalogeno-3,3-dimethylcyclopropylmethyl derivative of the formula

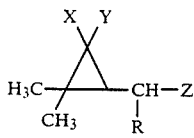

in which
X and Y each independently is halogen,
R is a hydrogen atom or a methyl group,
Z is a cyano group, a thiocyano group, a group of the formula

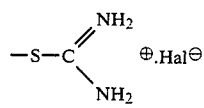

or a group of the formula

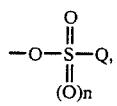

Hal is a halogen atom,
n is 0 or 1, and
Q is a lower alkyl group, a halo-lower alkyl group, a phenyl group, or a phenyl group substituted by at least one of halogen, lower alkyl and nitro.

2. A compound according to claim 1, in which X and Y each is chlorine, and Q, if present, is a methyl group, a halomethyl group, a phenyl group, or a phenyl group substituted by at least one of chloro, methyl and nitro.

3. A compound according to claim 1, in which said compound is 2,2-dichlor-3,3-dimethylcyclopropylmethyl thiocyanate of the formula

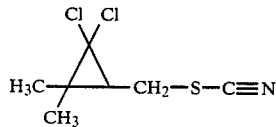

4. A compound according to claim 1, in which said compound is S-(2,2-dichloro-3,3-dimethylcyclopropylmethyl)isothiouronium bromide

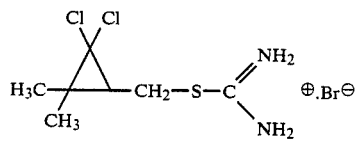

5. A compound according to claim 1, in which said compound is 2,2-dichloro-3,3-dimethylcyclopropylmethyl p-toluenesulfonate of the formula

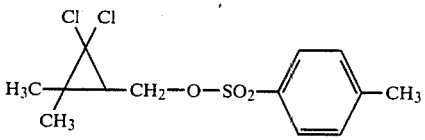

6. A compound according to claim 1, in which said compound is 2,2-dichloro-3,3-dimethylcyclopropylmethyl methanesulfonate of the formula

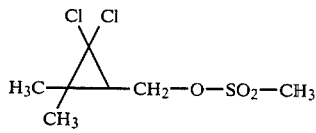

7. A compound according to claim 1, in which said compound is 2,2-dichloro-3,3-dimethylcyclopropylmethyl benzenesulfonate of the formula

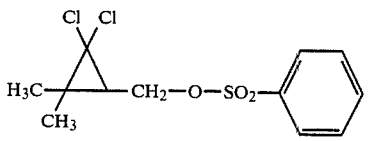

8. A compound according to claim 1, in which said compound is 1-(2,2-dichloro-3,3-dimethylcyclopropyl)ethyl benzenesulfonate of the formula

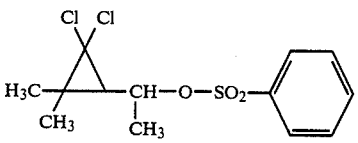

9. A compound according to claim 1, in which said compound is 1-(2,2-dichloro-3,3-dimethylcyclopropyl)ethyl p-toluenesulfonate of the formula

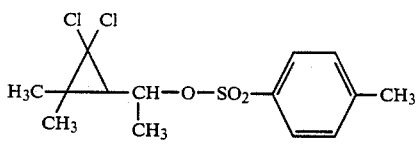

10. A compound according to claim 1, in which said compound is 2,2-dichloro-3,3-dimethylcyclopropylacetonitrile of the formula

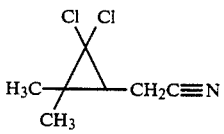

11. A fungicidal composition comprising a fungicidally effective amount of a compound according to claim 1 in admixture with a carrier.

12. A method of combating fungi which comprises administering to such fungi or to a habitat thereof a fungicidally effective amount of a compound according to claim 1.

13. The method according to claim 12 wherein such compound is 2,2-dichloro-3,3-dimethylcyclopropylmethyl thiocyanante, S-(2,2-dichloro-3,3-dimethylcyclopropylmethyl)isothiouronium bromide, 2,2-dichloro-3,3-dimethylcyclopropylmethyl p-toluenesulfonate, 2,2-dichloro-3,3-dimethylcyclopropylmethyl methylsulfonate, 2,2-dichloro-3,3-dimethylcyclopropylmethyl benzenesulfonate, 1-(2,2-dichloro-3,3-dimethylcyclopropyl)-ethyl benzenesulfonate, 1-(2,2-dichloro-3,3-dimethylcyclopropyl)-ethyl p-toluenesulfonate or 2,2-dichloro-3,3-dimethylcyclopropylacetonitrile.

* * * * *